United States Patent [19]

Mandl et al.

[11] Patent Number: 5,525,903
[45] Date of Patent: Jun. 11, 1996

[54] EDDY CURRENT METHOD OF ACQUIRING THE SURFACE LAYER PROPERTIES OF A METALLIC TARGET

[75] Inventors: Roland Mandl, Ortenburg; Axel Seikowsky, Pfarrkirchen; Andreas Spang, Türkismühle, all of Germany

[73] Assignee: Micro-Epsilon Messtechnik GmbH & Co. KG, Ortenburg, Germany

[21] Appl. No.: 292,364

[22] Filed: Aug. 18, 1994

[30] Foreign Application Priority Data

Aug. 18, 1993 [DE] Germany ............................ 43 27 712.8

[51] Int. Cl.$^6$ ............................ G01B 7/06; G01B 7/34; G01N 27/90
[52] U.S. Cl. ............................ 324/230; 324/226; 324/227; 324/238
[58] Field of Search ............................ 324/226, 227, 324/229–232, 234, 236–240, 207.16, 207.26, 671; 356/375, 376

[56] References Cited

U.S. PATENT DOCUMENTS

| 4,977,853 | 12/1990 | Falcoff et al. ............................ 324/230 |
| 5,355,083 | 10/1994 | George et al. ............................ 324/230 X |

FOREIGN PATENT DOCUMENTS

| 2923066 | 4/1981 | Germany. | |
| 257371 | 6/1988 | Germany. | |
| 4007363 | 3/1990 | Germany. | |
| 3217519 | 3/1992 | Germany. | |
| 0139602 | 8/1982 | Japan | 324/230 |
| 0002501 | 1/1991 | Japan | 324/230 |
| 0794359 | 1/1981 | U.S.S.R. | 324/230 |
| 0871056 | 10/1981 | U.S.S.R. | 324/230 |

Primary Examiner—Gerard R. Strecker
Attorney, Agent, or Firm—Bell, Seltzer, Park & Gibson

[57] ABSTRACT

A sensor arrangement and a method of acquiring properties of the surface layer (3) of a metallic target (2), which allow a nondestructive and substantially distance-independent measurement to be performed, with the requirements to be met by the sensor positioning being minimal. The sensor arrangement (1) comprises a combination of at least one eddy-current sensor (5) with at least one displacement measuring sensor (6), the depth of penetration of the eddy currents generated by the eddy-current sensor (5) corresponding to at least twice the thickness of the surface layer (3), and the displacement measuring sensor (6) serving to determine the distance of the sensor arrangement (1) from the target surface (4). The measuring signals of the eddy-current sensor (5) and the displacement measuring sensor (6) are evaluated on the basis of a hypothetical depth of penetration of the eddy currents, which is to be determined as a function of the frequency of the eddy currents and of the conductivity and permeability of the base material (8) of target (2).

13 Claims, 2 Drawing Sheets

EDDY CURRENT METHOD OF ACQUIRING THE SURFACE LAYER PROPERTIES OF A METALLIC TARGET

BACKGROUND OF THE INVENTION

The present invention relates to a sensor arrangement and a method of acquiring the surface layer properties of a metallic target, it being presumed that the conductivity and the permeability of the base metal of the target are known.

The acquisition of the surface layer properties of a metallic target is understood to include, for example, the examination of the homogeneity of the surface layer of the target, or also the detection of damage in the structure of the target surface. Special importance is attached to the application of the present invention in measuring coating thicknesses. In this instance, the target consists of a metallic base material and a coating or plating, which corresponds to the surface layer, and is preferably formed by a metallic material other than the base material. Thus, the base material serves as a carrier for the coating or surface layer. In practice, it is often necessary to determine the thickness of such a coating. However, this will turn out to be problematic, when the coating is not to be damaged during this process.

While methods of measuring the thickness are known for foils, strips, or the like of nonconductive materials, they are however not easily transferable to the measuring of the coating thickness of a metallic surface layer on a metallic base material either with respect to the sensors in use, or with respect to the method or the measuring principle underlying the method. This all the more, inasmuch as the method of measuring employed for a certain measuring application and in particular the types of sensors employed within the scope of this method are primarily selected in dependence on whether the layer, whose thickness is to be determined, consists of a conductive or a nonconductive material.

It is therefore the object of the present invention to provide a sensor arrangement and a method of acquiring surface layer properties of a metallic target, which permit a measurement to be performed that is nondestructive and as noncritical as possible with respect to the exactness of the sensor positioning.

SUMMARY OF THE INVENTION

The sensor arrangement of this invention, which allows the foregoing object to be realized, comprises the combination of at least one eddy-current sensor and one displacement measuring sensor, with the depth of penetration of the eddy currents generated by the eddy current sensor corresponding to at least twice the thickness of the surface layer, and with the displacement measuring sensor serving to determine the distance of the sensor arrangement from the surface of the target.

The method of the present invention is characterized in that the sensor arrangement is positioned with respect to the target surface such that the eddy currents generated by the eddy-current sensor penetrate at least the surface layer of the target, which is to be examined, that the use of the displacement measuring sensor allows the distance of the eddy current sensor from the target surface to be determined, and that the measuring signals of the eddy current sensor and the displacement measuring sensor are evaluated on the basis of a hypothetical penetration depth of the eddy currents, which is to be determined as a function of the frequency of the eddy currents and of the conductivity and permeability of the base material of the target.

To begin with, it has been recognized in accordance with the invention that the depth of penetration, also named skin depth, is dependent on high-frequency eddy currents in metal surfaces via the function $$\text{Skin depth [mm]} = 0.503 \cdot \sqrt{\sigma \frac{\left[\frac{\Omega \text{mm}^2}{\text{m}}\right]}{\mu_r \cdot f[\text{MHz}]}},$$

on the frequency of the eddy currents, the conductivity $\sigma$, and the permeability $\mu$. $\Omega$ in the above formula represents the physical unit "ohm" in the context of the physical unit for the conductivity. Thus, if the frequency f of the eddy currents generated by an eddy current sensor and the conductivity $\sigma$, as well as the permeability $\mu$ of a target are known, it will be possible to calculate the depth of penetration of the eddy currents generated by the eddy current sensor. Variations of an actually measured depth of penetration from the expected depth of penetration, which is calculated in advance, allow conclusions to be drawn as to the properties of the surface layer of the target, which is penetrated by the eddy currents. In accordance with the invention, it has also been found that a conversion of the above-described principle into a practicable measuring method will require the consideration of other factors, such as, for example, different positionings of the sensors, which vary randomly from measurement to measurement, and which should be considered in the evaluation of the measured values. To this end, the present invention proposes the use of a combination sensor, i.e., a sensor arrangement, which comprises at least one eddy-current sensor and at least one displacement measuring sensor. The use of the displacement measuring sensor allows the distance of the sensor arrangement, in particular the eddy current sensor, from the surface of the target to be determined in a simple manner. Finally, it has also been recognized that a particularly great reliability of the measurement will be achieved, when the expected depth of penetration of the eddy currents generated by the eddy-current sensor corresponds to at least twice the thickness of the surface layer.

There exist various possibilities of realizing the two types of sensors of the sensor arrangement. When selecting an eddy-current sensor, it is recommended to prefer such sensors, which are able to generate high-frequency eddy currents, since the above-specified functional relation between the depth of penetration or skin depth and the frequency of the eddy currents is given primarily for high-frequency eddy currents. Although a functional relation is presumed to exist likewise between the skin depth and the frequency of the eddy currents at a lower frequency, same is however less easily accessible to the evaluation.

Considered for use as a displacement measuring sensor are capacitive or also optical sensors. Regardless of the type of sensor, when it comes to select specific sensors, such having a rugged design or enclosure are to be preferred, since the sensor arrangement in accordance with the invention is normally moved, and should also be suitable for the contact with the target.

Likewise, with respect to the possible arrangements of the eddy-current sensor relative to one or more displacement measuring sensors, various advantageous possibilities are conceivable to realize the sensor arrangement of the present invention. Particularly advantageous is the arrangement of the eddy-current sensor and one displacement measuring sensor along one axis, since this arrangement effectively avoids a falsification of measuring signals, which may be caused by a tilting of the sensor arrangement. In the concrete case, it would be possible to arrange the capacitive or optical displacement measuring sensor in the interior of the coil of the eddy-current sensor and parallel to the axis of the coil. However, even when the sensors of the sensor arrangement are not positioned along one axis, but are arranged side by side, it will be possible to effectively prevent measuring errors resulting from a tilting of the sensor arrangement, in that several displacement measuring sensors are arranged substantially evenly distributed on the periphery of the eddy-current sensor. In this manner, it will be possible not only to detect a tilting, but to also consider same in the evaluation of the measuring value signals.

For the evaluation, it is possible to provide an evaluation unit spatially separated from the sensor arrangement. This measure offers itself always, when the target surface is hard to access. In this instance, it is suggested that the sensor arrangement be as small as possible, i.e. without additional units which enlarge the setup of the sensor arrangement, since for performing a measurement the sensor arrangement is either held against or pushed directly onto the target surface, it being always necessary to consider that the actual depth of penetration of the eddy currents generated by the eddy-current sensor of the sensor arrangement should correspond to at least twice the thickness of the surface to be examined.

As already indicated above, the method of the present invention permits different properties of the surface layer to be examined. For example, the target may consist of a single metallic material of a known conductivity and permeability. This means that the material of the surface layer is identical with the base material of the target. The method of the present invention allows inhomogeneities in the surface layer to determine, i.e. up to a certain depth starting from the target surface. Likewise, it is possible to detect damage in the structure of the target surface.

However, the target may also be a coated or plated object. An example is a brass roll plated with chromium. Thus, the target consists of the brass roll, which forms the base material, and the chrome plating, which is here described as surface layer. Both the conductivity and permeability of the base material and the conductivity and permeability of the surface material are presumed to be known. The method of this invention will then allow the thickness to be numerically calculated of the plating or the surface layer based on a functional relation between the frequency of the eddy currents generated by the eddy-current sensor and the conductivities and permeabilities of the base material and of the material constituting the surface layer. This method is especially advantageous to determine the thickness of the surface layer with the aid of a sensor arrangement in accordance with the invention, since the measurement occurs in a nondestructive manner. Furthermore, the measurement is substantially distance-independent, so that the requirements to be met with respect to the positioning of the sensor arrangement are only small. Since the material data are normally very well known, it is likewise unnecessary to calibrate the sensor arrangement. Finally, it should be mentioned that the method of the present invention can be applied both to ferromagnetic base materials and a nonferromagnetic or ferromagnetic surface layer and to nonferromagnetic base materials with a nonferromagnetic or ferromagnetic surface layer.

In connection with the description of the Figures, the functional relation between the thickness of the surface layer a, the frequency f of the eddy currents, and the conductivities $\sigma$ and permeabilities of the base material and the material constituting the surface layer will be described in more detail.

There exist various possibilities of configuring and further developing the subject matter of the present invention. To this end, one may refer to the description of two embodiments employing the teaching of this invention with reference to the drawing. Further, in conjunction with the drawing the model underlying the present invention is again explained.

DETAILED DESCRIPTION OF THE PREFERRED EMBODIMENTS

Figure 1:
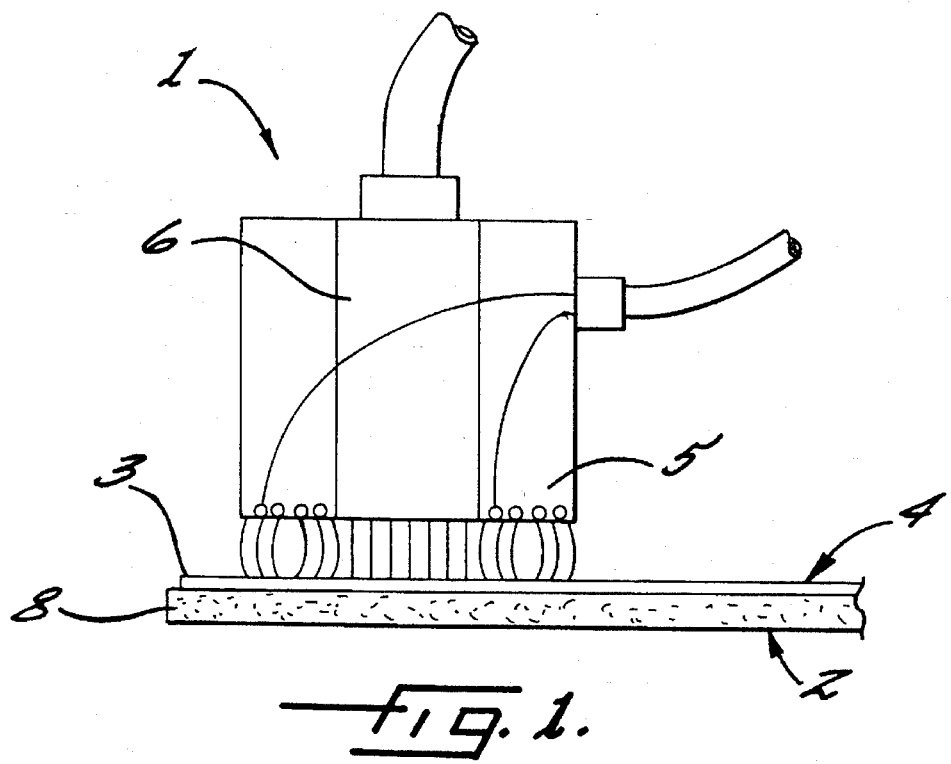
FIG. 1 is a schematic view of a first embodiment of a sensor arrangement in accordance with the invention.
Figure 2:
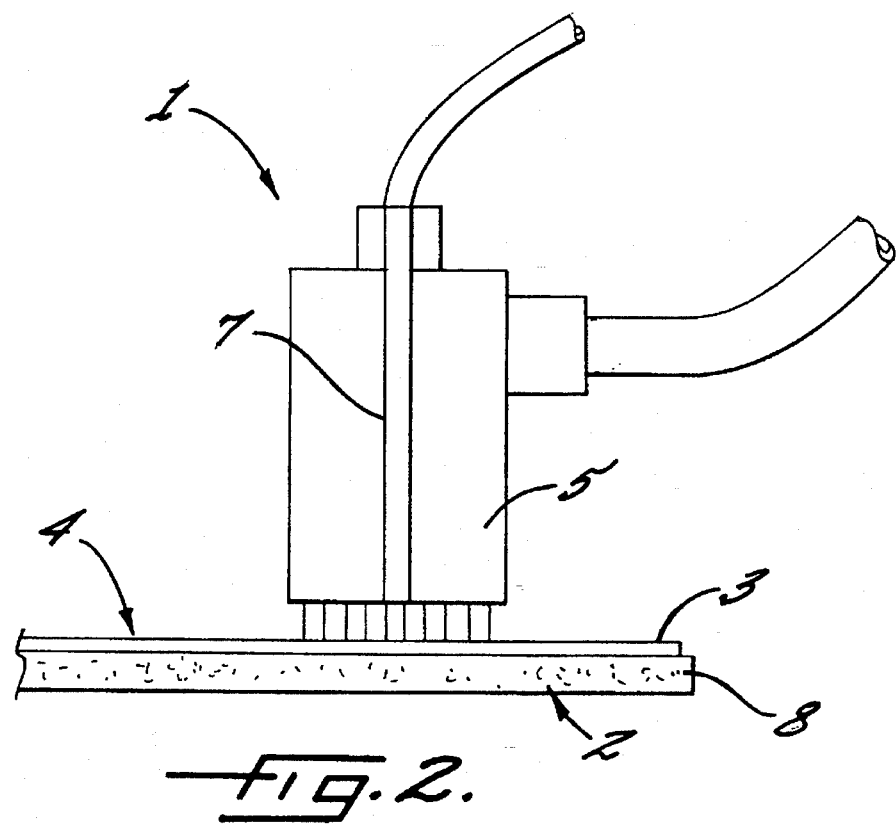
FIG. 2 is a schematic view of a second embodiment of a sensor arrangement in accordance with the invention.

FIGS. 1 and 2 each show a sensor arrangement 1, which extends at a distance from surface 4 of a target 2. In both illustrated embodiments, each target 2 consists of a base material 8 as well as a surface layer 3. The base material 8 forms practically a carrier, which is coated with surface layer 3. As already indicated, the target 2 consists of one or more different metallic materials. In the illustrated embodiments, the base material 8 differs from the material of surface layer 3. An example to name here for such a material combination is brass as base material and chromium as the material of the surface layer. Under certain conditions, which will be described below in more detail, it is likewise possible to use other material combinations.

In accordance with the invention, both sensor arrangements 1 illustrated in FIGS. 1 and 2 comprise a combination of an eddy-current sensor 5 with a displacement measuring sensor 6 or 7. The ideal depth of penetration of the eddy currents generated by eddy-current sensor 5 should correspond to at least twice the thickness of surface layer 3 of target 2. The displacement measuring sensor 6 or 7 serves to determine the distance of the entire sensor arrangement 1 from target surface 4. In fact, the displacement measuring sensor 6 or 7 measures its own distance from target surface 4. However, since one has to presume that the sensor arrangement is rigid, inasmuch as eddy-current sensor 5 and displacement measuring sensor 6 or 7 are arranged in a common rigid housing, it is possible to determine from the spacing between displacement measuring sensor 6 or 7 and target surface 4 both the distance of the entire sensor arrangement 1 from target surface 4 and the distance of eddy-current sensor 5 from target surface 4.

Eddy-current sensor 5 allows high-frequency eddy currents to be generated, as is described in more detail with reference to FIGS. 3 and 4.

The displacement measuring sensor shown in FIG. 1 is a displacement measuring sensor operating by capacitance, whereas displacement measuring sensor 7 shown in FIG. 2 operates by an optical measuring principle.

In both embodiments, eddy-current sensor 5 and displacement measuring sensor 6 or 7 are arranged along one axis, in that displacement measuring sensors 6 and 7 are each arranged in the interior of the coil of eddy-current sensor 5 and parallel to the coil axis.

The evaluation of the measuring signals of eddy-current sensor 5 and displacement measuring sensor 6 or 7 is greatly simplified in that the sensor combination formed by eddy current sensor 5 and displacement measuring sensor 6 or 7 is linearized or zero balanced relative to the base material 8 of the target. In this instance, it is particularly easy to determine and evaluate variations from an ideal expected measuring value.

Figure 3:
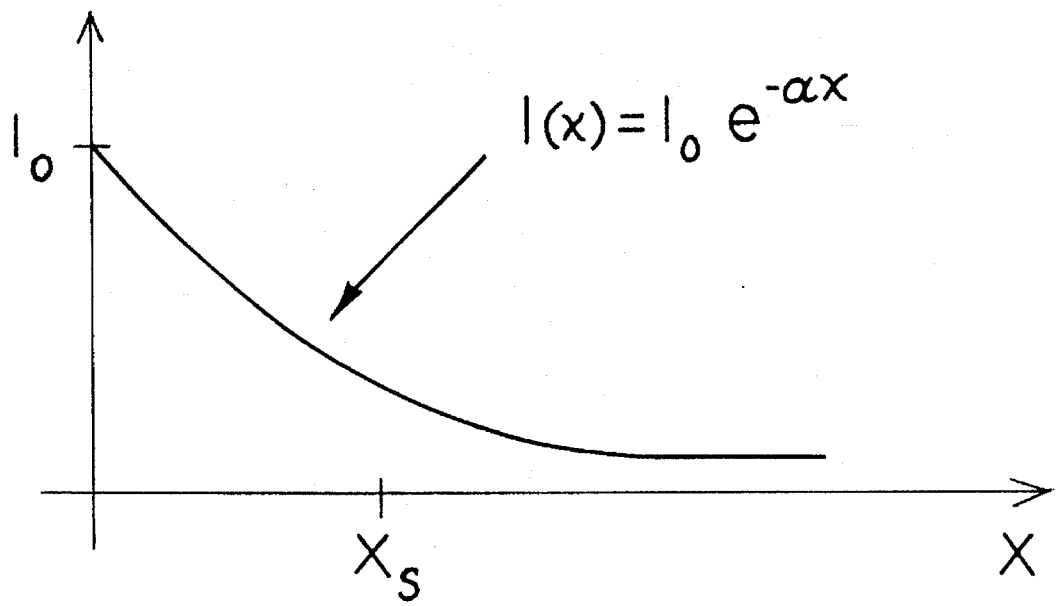
FIG. 3 illustrates the ideal current distribution in a metallic target of a homogeneous material.
Figure 4:
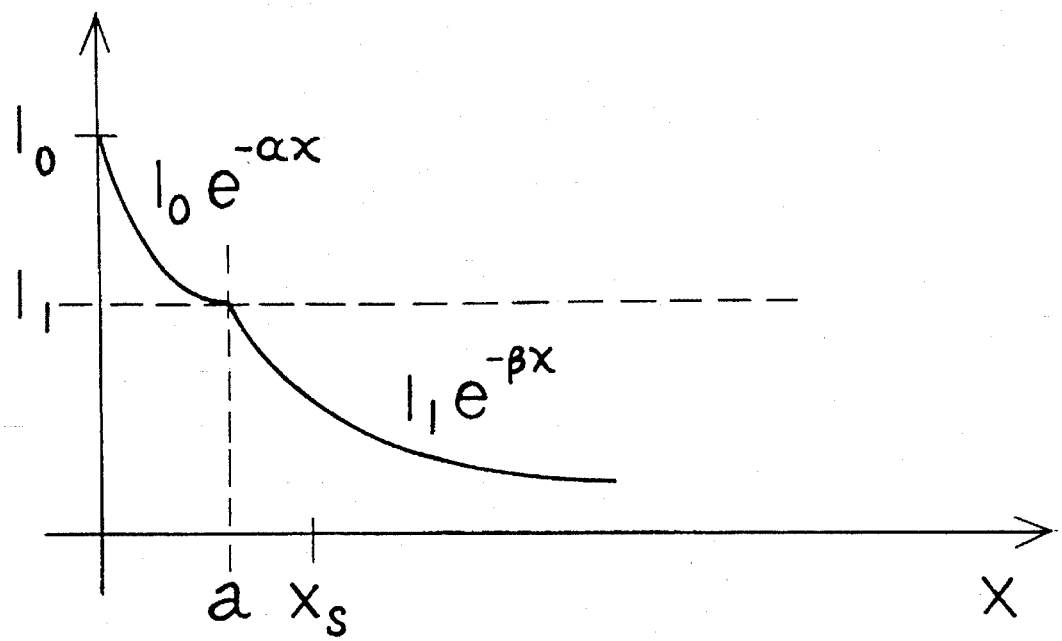
FIG. 4 illustrates the ideal current distribution in a target, with the material of the surface layer being different from that of the base layer of the target.

Having described and explained two advantageous possibilities of putting sensor arrangements to practice, the following will describe in more detail, with reference to FIGS. 3 and 4, the measuring principle which underlies the proposed method of measuring coating thicknesses.

Prerequisite for this thickness measurement of coatings of electrically conductive metals is that the combined metals possess different conductivities or vary in their relative permeability. Further, it is necessary that the coating thickness is thinner than twice to thrice the penetration depth of the eddy current sensor. This method allows accurate measurement of, for example, a thickness of 0.3 mm chromium on aluminum or another ferromagnetic or nonferromagnetic metal, i.e. up to an accuracy of 1 μm. To this end, a pair of sensors which is (thickness) linearized relative to the base material is held against or pushed onto the coating, with spacing variations up to 0.5 mm being insignificant or having only little importance. The measured values, which represent the depth of penetration under actual conditions, are compared with a hypothetical depth which is calculated assuming an ideal target of base material. This expected depth of penetration may be defined as "zero", and any deviation from this expected depth of penetration may be defined as "zero shift". This shift of the measured value is mathematically related to the ratio of conductivity of the combined materials and to the thickness of the coating.

As already indicated above, there exists the following relation between the depth of penetration or skin depth of high-frequency eddy currents in metal surfaces and the frequency f of these eddy currents, the conductivity σ, and the permeability μ:

$$\text{Skin depth [mm]} = 0.503 \cdot \sqrt{\sigma \frac{\left[\frac{\Omega mm^2}{m}\right]}{\mu_r \cdot f[MHz]}}$$

From this, there results a current distribution on the surface, as is illustrated in FIG. 3. Thus, in reality the eddy-current sensor does not measure against the surface of the metal, but against a point, which depending on the skin depth lies more or less deep in the metal and is indicated at $x_s$.

In a model calculation, this point may be assumed, for example, as the gravity $x_s$ of the current distribution function (in so doing, observations of the reflection damping and near-field observations are neglected). The gravity $x_s$ of a function, especially of the current distribution given in FIGS. 3 and 4, is the result of an evaluation analogous to the evaluation of the gravity of a mass distribution, and may be defined as $$x_s = \frac{\int l(x) \, x \, dx}{\int l(x) \, dx}$$

A laminated structure of the target results in a corresponding model. The current distribution of this model is shown in FIG. 4. Likewise in this instance, the coordinate of gravity $x_s$ is a function of he coating thickness a and the two skin depths α and β. From this functional relation, it is possible to calculate numerically the coating thickness a. Before dealing with this calculation in more detail, it should be mentioned that the experimentally determined response comes very close to the described model. Smaller variations are to be explained by the adjustment of the sensor on the flank of the resonance curve and the simplifications assumed in the model. Noteworthy is the little change in the linearity curve when measuring against nonferromagnetic metals of a greatly varying conductivity with a clear zero (gravity) shift of about 160 μm.

The second sensor, namely the displacement measuring sensor, which measures against the surface of the target, for example, by capacitance or optically, and which advantageously is arranged along the same axis as the eddy-current sensor, allows the conductivity of the metal or the thickness of the coating to be calculated by forming the difference of the two measured distances. Depending on the adjustment of the eddy-current sensor, the following realizable measuring methods are obtained:

1. Coating thickness measurement

|  | Nonferromagnetic layer | Ferromagnetic layer |
| --- | --- | --- |
| Ferromagnetic carrier | Layers ≦ 2 skin depth | Layers ≦ 2 skin depth Double sheet detection |
| Nonferrogmagnetic carrier | Layers ≦ 2 skin depth Double sheet detection | Layers ≦ 2 skin depth |

2. Conductivity measurement of metals (homogeneity); and

3. Detection of damage in the structure of the metal surface up to a depth which is smaller than the double skin depth.

The measurement according to the present invention includes the determination of the measuring signal of the eddy-current sensor on the one hand, which is represented by d, and the measuring signal of the displacement measuring sensor on the other hand, which is represented by $d_{ref}$. The calculation of the zero shift n is done by calculating the difference of the two measured distances d and $d_{ref}$, considering the geometrical sensor construction constant c and a linearity correction represented by the function $k(d,d_{ref})$. The latter function is defined in German patent application DE 40 11 717 A1. Thus, the zero shift n is calculated as follows:

$$n = d - d_{ref} + c + K(d, d_{ref}).$$

Taking into account the characteristic data of the sensors and the electronics, it is now possible to calculate from the zero shift a gravity shift $x_s$ in accordance with the above-described model:

$$x_s = c_1 n + c_2.$$

It should be noted that $c_1$ and $c_2$ are two circuit-dependent constants, which are empirically determined. Thus, $x_s$ is obtained from these circuit-dependent constants $c_1$ and $c_2$ and the measured value n. However, it further applies that $x_s$ is a function of the skin depths $\alpha$ and $\beta$ of the coating and of the carrier metal as well as the coating thickness a.

$$x_s = \frac{a(-\alpha\beta^2 e^{-\alpha a} + \alpha^2 \beta e^{-\alpha a - \beta a}) + \beta^2(1 - e^{-\alpha a}) + \alpha^2 e^{-\alpha a - \beta a}}{\alpha\beta^2(1 - e^{-\alpha a}) + \alpha^2 \beta e^{-\alpha a - \beta a}}$$

The foregoing formula can now be solved numerically for a.

In conclusion, it should be pointed out that the novel measuring method of the present invention is not restricted to the measuring of the thickness of coating layers on a target, but can also be used for the examination of the homogeneity of the surface layer of the target, or for the detection of damage to the structure of the target surface, because all these modifications of the target surface result in variations of the skin depth.

That which is claimed:

1. A method of acquiring properties of a surface layer (3) of a metallic target (2) which comprises a base material (8) and the surface layer (3), with the conductivity and permeability of the base material (8) and the surface layer (3) of the metallic target (2) being known, and comprising the steps of estimating the thickness of the surface layer (3) to be tested, positioning a sensor (1), which comprises at least one eddy current sensor (5) which is operable at a variable frequency and at least one displacement measuring sensor (6, 7) adjacent the target (2) so that the displacement measuring sensor (6) serves to determine the distance between the sensor (1) and the outer surface of the surface layer (3), determining a frequency of the eddy current sensor (5), based upon the known conductivity and permeability of the base material (8) and the surface layer (3) and the estimated thickness of the surface layer (3), which under ideal conditions would cause the eddy current to penetrate to an expected depth which is at least equal to the estimated thickness of the surface layer (3), operating the sensor (1) so that the eddy current sensor (5) operates at the determined frequency, and evaluating any difference between the actual penetration of the eddy current sensor (5) as measured by the sensor (1) and the expected depth of penetration.

2. The method as defined in claim 1 wherein the surface layer (3) comprises a material different from that of the base material (8).

3. The method as defined in claim 1 wherein the surface layer (3) comprises the same material as that of the base material (8).

4. The method as defined in claim 1 wherein the step of determining a frequency of the eddy current sensor includes determining a frequency which under ideal conditions would cause the eddy current to penetrate to an expected depth which is at least twice the estimated thickness of the surface layer (3).

5. The method as defined in claim 1 wherein the displacement measuring sensor (6) operates by capacitance.

6. The method as defined in claim 1 wherein the displacement measuring sensor (7) operates by an optical measuring principle.

7. The method as defined in claim 1 wherein the eddy current sensor (5) and the displacement measuring sensor (6, 7) are arranged along a common axis.

8. The method as defined in claim 1 wherein the eddy current sensor (5) and the displacement measuring sensor (6, 7) are arranged side by side.

9. The method as defined in claim 1 wherein said sensor (1) comprises a plurality of said displacement measuring sensors (6, 7) which are arranged substantially evenly distributed about the periphery of said eddy-current sensor (5).

10. The method as defined in claim 1 wherein said sensor (1) is zero balanced relative to the base material (8) of the target.

11. The method as defined in claim 1 wherein the evaluation step includes measuring the thickness of the surface layer (3) of the metallic target (2).

12. The method as defined in claim 1 wherein the positioning step includes positioning the sensor (1) directly against the target (2).

13. The method as defined in claim 1 wherein the positioning step includes supporting the sensor (1) at a distance spaced from the target (2).

* * * * *